United States Patent [19]
Gries et al.

[11] Patent Number: 5,843,399
[45] Date of Patent: Dec. 1, 1998

[54] DTPA MONOAMIDES FOR MRI

[75] Inventors: Heinz Gries; Erich Klieger; Bernd Radüchel; Heribert Schmitt-Willich; Hanns-Joachim Weinmann; Hubert Vogler; Gabriele Schuhmann-Giampieri; Jürgen Conrad, all of Berlin, Germany

[73] Assignee: Schering Aktiengesellschaft, Germany

[21] Appl. No.: 484,317

[22] Filed: Jun. 7, 1995

Related U.S. Application Data

[62] Division of Ser. No. 228,524, Apr. 15, 1994, which is a continuation of Ser. No. 681,682, Apr. 8, 1991, abandoned.

[30] Foreign Application Priority Data

Apr. 6, 1990 [DE] Germany .......... 40 11 684.0

[51] Int. Cl.⁶ .......... A61B 5/055; A61K 49/04
[52] U.S. Cl. .......... 424/1.65; 424/9.365; 424/942; 514/836
[58] Field of Search .......... 424/1.65, 9.365, 424/9.42; 514/836; 128/653.4, 654; 436/173

[56] References Cited

U.S. PATENT DOCUMENTS

| | | | |
|---|---|---|---|
| 4,352,751 | 10/1982 | Wieder et al. | 260/112 |
| 4,647,447 | 3/1987 | Gries et al. | 424/9 |
| 4,687,659 | 8/1987 | Quay | 424/9 |
| 4,826,673 | 5/1989 | Dean et al. | 424/9 |
| 4,859,451 | 8/1989 | Quay et al. | 424/9 |
| 4,994,259 | 2/1991 | Rocklage et al. | 424/9 |
| 5,011,925 | 4/1991 | Rajagopalan et al. | 544/58.1 |
| 5,039,512 | 8/1991 | Kraft et al. | 424/9 |
| 5,077,037 | 12/1991 | Wallace | 424/9 |
| 5,087,439 | 2/1992 | Quay | 424/9 |
| 5,087,440 | 2/1992 | Chacheris et al. | 424/9 |
| 5,098,692 | 3/1992 | Gries et al. | 424/9 |
| 5,137,711 | 8/1992 | Weber et al. | 424/9 |
| 5,198,208 | 3/1993 | Berg et al. | 424/1.1 |
| 5,281,704 | 1/1994 | Love et al. | 540/465 |
| 5,316,756 | 5/1994 | Gries et al. | 424/9 |
| 5,330,743 | 7/1994 | Gibby et al. | 424/9 |
| 5,362,475 | 11/1994 | Gries et al. | 424/9 |
| 5,376,358 | 12/1994 | Rajagopalan et al. | 424/9 |
| 5,384,108 | 1/1995 | Rajagopalan et al. | 424/9 |
| 5,399,340 | 3/1995 | Radüchel et al. | 424/9 |
| 5,453,264 | 9/1995 | Mori et al. | 424/9.364 |

FOREIGN PATENT DOCUMENTS

| | | |
|---|---|---|
| 0 243 929 | 11/1987 | European Pat. Off. . |
| 0 258 616 | 3/1988 | European Pat. Off. . |
| 0 263 059 | 4/1988 | European Pat. Off. . |
| 0 299 795 | 1/1989 | European Pat. Off. . |
| 90/01024 | 2/1990 | WIPO . |
| 90/08138 | 7/1990 | WIPO . |

*Primary Examiner*—Gary E. Hollinden
*Attorney, Agent, or Firm*—Millen, White, Zelano & Branigan, P.C.

[57] ABSTRACT

Chelate compounds of general formula I

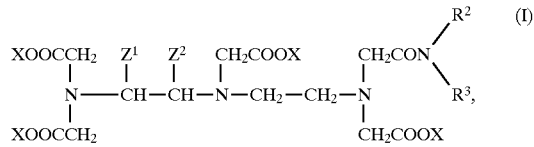

wherein

X is a hydrogen atom and/or a metal ion equivalent of an element of atomic numbers 21–29, 31, 32, 37–40, 42–44, 49 or 57–83, and $Z^1, Z^2, R^1, R^2, R^3$ and $R^4$ are as defined herein, as well as their salts with inorganic and/or organic bases, amino acids or amino acid amides, are valuable pharmaceutical agents, e.g., for NMR imaging.

18 Claims, 2 Drawing Sheets

DTPA MONOAMIDES FOR MRI

This is a division of application Ser. No. 08/228,524 filed Apr. 15, 1994, which is a continuation of Ser. No. 07/681,682, filed Apr. 8, 1991 (abandoned).

The invention relates to new diethylenetriaminepentaacetic acid (DTPA) monoamides, DTPA monoamide complexes and complex salts, agents containing these compounds, their use in the NMR diagnosis as well as the process for the production of these compounds and agents.

At the beginning of the fifties, metal complexes were already under consideration as contrast media for radiology. But the compounds used at that time were so toxic that a use in humans was out of the question. It was therefore really surprising that certain complex salts proved sufficiently compatible so that a routine use in humans for diagnostic purposes could be taken into consideration. As a first representative of this family of substances, the dimeglumine salt of the Gd DTPA (gadolinium(III) complex of diethylenetriaminepentaacetic acid) described in the European patent application with publication number 71564 has proven itself very well as a contrast medium for nuclear spin tomography. It has been registered worldwide as the first NMR diagnostic agent under the name Magnevist®.

Magnevist® is especially well-suited for the diagnosis of pathological areas (e.g., inflammations, tumors, infarctions, etc.). After intravenous injection, the compound spreads extracellularly and is eliminated by glomerular secretion through the kidneys. Passage of intact cell membranes and extrarenal elimination are practically not observed.

Contrast media, which exhibit at least a partially extrarenal elimination, were desirable especially for patients with limited kidney function, in which Magnevist® is eliminated only very slowly and can be removed partially from the organism only with the help of a dialyzer.

Therefore, there is a need for NMR contrast media which show a pharmacokinetic behavior other than that of Magnevist®.

This invention makes available such compounds and agents as well as to provide a process for their production.

It has been found that the compounds according to the invention surprisingly show the desired properties: both renal elimination and excretion with the feces after parenteral administration. But, surprisingly, the elimination through the gallbladder is not the only method of extrarenal elimination: in the case of NMR tests in rats, a contrast enhancement of the gastrointestinal tract was also unexpectedly observed after intravenous administration of the compounds according to the invention, e.g., these compounds are suitable both for the organ-specific NMR diagnosis of the hepatobiliary system and the stomach. The kidneys as well as implanted tumors are optionally contrasted.

Surprisingly, the complex compounds according to the invention are also resorbed after oral administration and then are eliminated through the hepatobiliary system, i.e., they are suitable as oral liver contrast media.

Such a phenomenon was not previously described of any contrast medium for nuclear spin tomography. The elimination (secretion) through the stomach has the advantage that a differentiation of abdominal structures (e.g., pancreas) from the gastrointestinal tract is made possible with simultaneous contrast enhancement of pathological processes (tumors, inflammations). A representation of the renal system, the liver and the gallbladder and biliary tract as well as the lymph nodes can, moreover, also be achieved. Besides the improved representation of ulcers and stomach cancers, a study of the gastric secretion can also be performed with the help of the imaging processes.

By the use of the above-mentioned compounds—in addition to the diagnosis of the hepatobiliary system—patients suffering from both renal insufficiencies and gastrointestinal diseases (at least 10% of the population in the western industrialized countries) thus can be helped. Most of these patients, as well as a large number of patients suspected of having such a disease, have to undergo diagnostic tests. Two suitable methods in this respect for gastrointestinal diseases above all are now customary: endoscopy and X-ray diagnosis with the help of barium contrast media.

These tests exhibit different drawbacks: they are affected by the risk of the radiation exposure, trauma-causing, connected with inconveniences, occasionally even with risks for the patients, and can therefore cause psychological stress. They mostly have to be performed repeatedly, are relatively expensive to perform, require the active cooperation of the patient (e.g., taking a certain posture), and often cannot be used with infirm or with high-risk patients.

The object, to make available new diagnostic methods to recognize and localize gastrointestinal diseases which do not have these drawbacks, is therefore also achieved by the use of the above-mentioned complex compounds and agents.

Also, without specific measures, their pharmacokinetics makes possible the improvement of the diagnosis of numerous diseases. The complexes are unchanged for the most part and are again eliminated quickly, so that no harmful effects are observed especially also in the case of the use of relatively toxic metal ions even in the case of high dosages.

The practical use of the new complexes is also facilitated by their advantageous chemical stability.

The compounds according to the invention are characterized by general formula I:

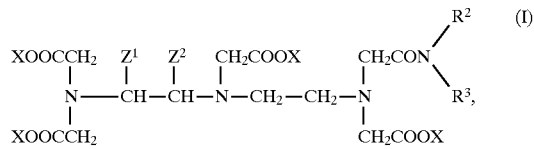

in which $Z^1$ and $Z^2$ each stand for a hydrogen atom or the radical $-(CH_2)_m-(C_6H_4)_q-(O)_k-(CH_2)_n-(C_6H_4)_l-(O)_r-R$, in which m and n independently mean numbers 0–20, k, l, q and r independently mean numbers 0 and 1 and R means a hydrogen atom, an optionally $OR^1$-substituted $C_1-C_6$ alkyl radical or a $CH_2COOR^1$ group with $R^1$ meaning a hydrogen atom, a $C_1-C_6$ alkyl radical or a benzyl group, $R^2$ stands for a saturated, unsaturated, straight-chain or branched-chain or cyclic non-aromatic hydrocarbyl group with up to 20 C-atoms, an aryl group (e.g., of up to 10 C-atoms) or aralkyl group (e.g., of up to 16 C-atoms), all substituted by a carboxyl group or a sulfone group, each optionally esterified with a $C_1-C_6$ alkyl radical or benzyl radical, $R^3$ stands for a hydrogen atom or for a saturated, unsaturated, straight-chain or branched-chain or cyclic non-aromatic hydrocarbyl, e.g., alkyl group with up to 20 C-atoms, an aryl group (e.g., of up to 10 C-atoms) or aralkyl group (e.g., of up to 16 C-atoms), all optionally substituted by a carboxyl group or sulfone group, each optionally esterified with a $C_1-C_6$ alkyl radical or benzyl radical, X stands for a hydrogen atom and/or a metal ion equivalent of an element of atomic numbers 21–29, 31, 32, 37–40, 42–44, 49 or 57–83, provided that at least one of substituents $Z^1$ and $Z^2$ stands for a hydrogen atom, that—if n and l each stand for the number 0–k and r are not the number 1 at the same time and that the radical of the acid groups is optionally present as an ester or amide, as well as their salts with inorganic and/or organic bases, amino acids or amino acid amides.

Compounds of general formula I with X meaning hydrogen are designated as complexing agents and, with at least two of substituents X meaning a metal ion equivalent, they are designated as metal complexes.

The element of the above-mentioned atomic number, which forms the central ion of the physiologically compatible complex salt can, of course, also be radioactive for the desired purpose of the diagnostic agent according to the invention.

Thus, if the agent according to the invention is intended for use in NMR diagnosis, the central ion of the complex salt has to be paramagnetic. These are in particular the divalent and trivalent ions of the elements of atomic numbers 21–29, 42, 44 and 58–70. Suitable ions are, for example, the chromium(III), manganese(II), iron(II), cobalt(II), nickel (II), copper(II), praseodymium(III), neodymium(III), samarium(III), and ytterbium(III) ion. Because of their very strong magnetic moment, the gadolinium(III), terbium(III), dysprosium(III), holmium(III), erbium(III), and iron(III) ions are especially preferred.

The central ion has to be radioactive for the use of the agents according to the invention in nuclear medicine. For example, radioisotopes of the elements copper, cobalt, gallium, germanium, yttrium, strontium, technetium, indium, ytterbium, gadolinium, samarium and iridium are suitable.

Thus, if the agent according to the invention is intended for use in the X-ray diagnosis, the central ion has to be derived from an element of a higher atomic number to achieve a sufficient absorption of the X-rays. It has been found that, for this purpose, diagnostic agents, which contain a physiologically compatible complex salt with central ions from elements of atomic numbers between 21–29, 42, 44, 57–83, are suitable; these are, for example, the lanthanum(III) ion and the above-mentioned ions of the lanthanide group.

The numbers standing for m and n are preferably 0 to 5.

As the hydrocarbon portions of R, $R^1$ and $R^2$, straight-chain or branched hydrocarbons, especially alkyl groups, all with up to 6 carbon atoms, preferably up to 4 carbon atoms, which are optionally substituted in the case of R by one or more, preferably 1 to 3, hydroxy groups or $C_1$–$C_6$ alkoxy groups, preferably $C_1$–$C_4$ alkoxy groups, are suitable.

As optionally substituted alkyl groups, for example, there can be mentioned the methyl, hydroxymethyl, ethyl, 2-hydroxyethyl, 2-hydroxy-1-(hydroxymethyl)-ethyl, 1-(hydroxymethyl)-ethyl, propyl, isopropyl, 2- and 3-hydroxypropyl, 2,3-dihydroxypropyl, n-, sec-, and tert-butyl, 2-, 3-, and 4-hydroxybutyl, 2- and 3-hydroxyisobutyl, pentyl, 2-, 3-, and 4-hydroxy-2-methylbutyl, 2,3,4-trihydroxybutyl, 1,2,4-trihydroxybutyl, cyclopentyl, cyclohexyl, 2,3,4,5,6-pentahydroxyhexyl group as well as—in the case of the hydroxyalkyl groups—their $C_1$–$C_6$ alkyl derivatives, preferably $C_1$–$C_4$ alkyl derivatives, i.e., OH groups where the H-atom is replaced by said groups.

As preferred aryl group and aralkyl groups $R^2$ and $R^3$, there can be mentioned the phenyl, benzyl, and isopropylphenyl radicals.

Preferred substituents $Z^1$ or $Z^2$ are the —$CH_2$—$C_6H_4$—OH, —$CH_2$—$C_6H_4$—$OCH_3$, —$CH_2C_6H_5$, —$CH_2$—$C_6H_4$—O—$CH_2$—$C_6H_4$—$OCH_3$, —$CH_2$—O—$CH_2$—$C_6H_5$, —$CH_2$—$C_6H_4$—O—$CH_2$—COOH, —$CH_2$—$C_6H_4$—$OC_2H_5$, —$CH_2$—$C_6H_4$—$OC_4H_9$, —$CH_2$—$C_6H_4$—O—$CH_2$—$C_6H_5$ radical.

Above and below, the substituents can be placed on any C-atom of the main group to which they are attached. Typically, there are 1–6 OR' substituents, preferably up to one per C-atom.

Saturated, unsaturated, straight-chain, branched-chain or cyclic hydrocarbyl, e.g., alkyl groups, with up to 20 C-atoms, preferably with 5 to 18 C-atoms, aryl groups and aralkyl groups are suitable as radicals $R^2$ and $R^3$, in each case substituted ($R^2$) or optionally substituted ($R^3$) by a carboxyl group or sulfone group, optionally esterified with a $C_1$–$C_6$ alkyl radical, preferably $C_1$–$C_4$ alkyl, or benzyl radical.

For example, there can be mentioned the methyl, ethyl, propyl, isopropyl, butyl, pentyl, hexyl, phenyl, benzyl, 4-carboxy-phenylene, 1-cyclohexyl-1-carboxylic acid, 1-cyclopentyl-1-carboxylic acid, 2-carboxyphenylene, 11-carboxy-1-undecyl, 10-carboxy-1-decyl, 7-carboxy-1-heptyl, 6-carboxy-1-hexyl, 5-carboxy-1-pentyl, 4-carboxybenzyl, 4-carboxy-1-cyclohexylmethyl, 4-carboxymethylphenylene, 4-(1,1-dimethylcarboxymethylene)-phenylene, 4-sulfophenylene, 10-sulfo-1-decyl, 8-sulfo-1-octyl, 17-carboxy-7-heptadecyl, 7-carboxy- 2-heptyl, 1-carboxy-4-phenyl-2-propyl, 2-carboxyethyl, 4-carboxy-4-but-1-enyl radicals.

The residual acidic hydrogen atoms, i.e., those which have not been substituted by the central ion, can optionally be replaced completely or partially by cations of inorganic and/or organic bases or amino acids. The corresponding acid groups can also be converted completely or partially to esters or amides.

Suitable inorganic cations are, for example, the lithium ion, the potassium ion, the calcium ion, the magnesium ion and in particular the sodium ion. Suitable cations of organic bases are, among others, those of primary, secondary or tertiary amines, such as, for example, ethanolamine, diethanolamine, morpholine, glucamine, N,N-dimethylglucamine and in particular N-methylglucamine. Suitable cations of amino acids are, for example, those of lysine, arginine and ornithine as well as the amides of the otherwise acid or neutral amino acids.

Suitable esters are preferably those with a $C_1$–$C_6$ alkyl radical: for example, there can be mentioned the methyl, ethyl, and tert-butyl, benzyl, and 4-methoxybenzyl radical.

Thus, if the carboxylic acid groups are to be present at least partially as amides, saturated, unsaturated, straight-chain or branched-chain or cyclic hydrocarbons with up to 5 C-atoms are suitable as radicals, which are optionally substituted by 1 to 3 hydroxy groups or $C_1$–$C_4$ alkoxy groups. For example, there can be mentioned the methyl, ethyl, 2-hydroxyethyl, 2-hydroxy-1-(hydroxymethyl)-ethyl, 1-(hydroxymethyl)-ethyl, propyl, isopropenyl, 2-hydroxypropyl, 3-hydroxypropyl, 2,3-dihydroxypropyl, butyl, isobutyl, isobutenyl, 2-hydroxybutyl, 3-hydroxybutyl, 4-hydroxybutyl, 2,3,4-hydroxy-2-methylbutyl, 2- and 3-hydroxyisobutyl, 2,3,4-trihydroxybutyl, 1,2,4-trihydroxybutyl, pentyl, cyclopentyl, and 2-methoxyethyl group. The amide radical can also be a heterocyclic 5- or 6-ring formed with the inclusion of the amide-nitrogen. By way of example, there can be mentioned: the pyrrolidinyl, piperidyl, pyrazolidinyl, pyrrolinyl, pyrazolinyl, piperazinyl, morpholinyl, imidazolidinyl, oxazolidinyl, thiazolidinyl ring.

The compounds according to the invention exhibit the initially described desired properties. Moreover, the compatibility of the monoamides according to the invention is surprisingly increased in comparison with the corresponding bisamides. Thus, for example, the $LD_{50}$ value (rat) of the compound of Example 1b) (preferred for use in imaging the hepatobiliary system, e.g., the liner) is higher by the factor 3 than the corresponding value of the previously known (DE-OS 34 01 052.1, Example 2) bisamide. However, based on the prior art, a falling off of the $LD_{50}$ value was to be expected: thus, for example, the $LD_{50}$(mouse) value or $LD_{50}$(rat) value of the bisamide gadolinium complex of $N^6$-carboxymethyl-$N^3$,$N^9$-bis(2,3-dihydroxypropyl-N-methyl-carbamoylmethyl)-3,6,9-triazaundecanedioic acid [European Patent Publication No. 0 130 934, Example 6a)] drops by 50 or 30% in the case of the corresponding monoamide (formula I, $Z^1=Z^2=M$, $R^2=$—$CH_2CH(OH)$ $CH_2OH$, $R^3=CH_3$).

The introduction of amide groups for the production of complexing agents, i.e. of compounds of general formula I with X meaning hydrogen, takes place by partial conversion of activated carboxyl groups into amide groups of—corresponding to the desired end product—suitable pentacarboxylic acids each. For this process, all synthesis possibilities known to one skilled in the art are suitable.

An example for this purpose is the reaction of the anhydrides or esters of general formulas II and III

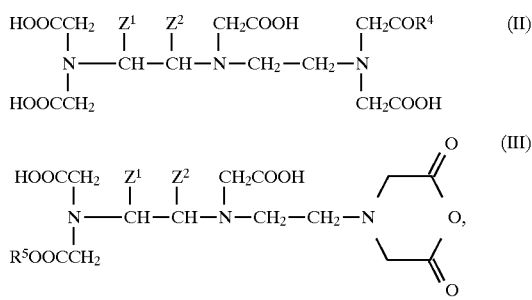

in which $Z^1$ and $Z^2$ have the above-indicated meanings, $R^4$ stands for the radical of an activated carbonyl group or for $OR^5$ and $R^5$ represents a hydrogen atom or a $C_1$–$C_6$ alkyl radical, with amino acids of general formula IV

in which $R^2$ and $R^3$ have the above-mentioned meanings.

As examples for an activated carbonyl group, there are cited mixed anhydride (with, e.g., chloroformic acid ester) and the addition product on carbodiimides, e.g., dicyclohexylcarbodiimide (DCC).

As suitable amino acids, for example, there can be mentioned:
4-aminobenzoic acid, 1-aminocyclohexane-1-carboxylic acid, 1-aminocyclopentane-1-carboxylic acid, 2-aminobenzoic acid, 12-aminododecanoic acid, 11-aminoundecanoic acid, 8-aminooctanoic acid, 7-aminoheptanoic acid, 6-aminohexanoic acid, 4-aminomethylbenzoic acid, trans-4-(aminomethyl)-cyclohexanecarboxylic acid, p-aminophenylacetic acid, alpha,alpha-dimethyl-p-aminophenylacetic acid, sulfanilic acid, 10-aminodecane-1-sulfonic acid, 8-aminooctane-1-sulfonic acid, 12-aminooctadecanoic acid, 2-aminooctanoic acid, 2-amino-4-phenylbutyric acid, iminodiethanoic acid, N-methylaminobenzene-4-sulfonic acid, 12-methylaminododecanoic acid, 2-amino-4-pentenoic acid.

The saponification of optionally still present ester groups takes place according to the processes known to one skilled in the art, for example by alkaline hydrolysis.

The production of the monoanhydrides of general formula III with $R^5=C_1$–$C_6$ alkyl radical is to be described by the example of the monoanhydride of diethylenetriaminepentaacetic acid ethyl ester, starting from the monoethyl ester of DTPA (J. Pharm. Sci. 68, 1979, 194):

The production of the monoanhydrides of general formula III with $R^5=H$ takes place according to the methods known to one skilled in the art (cf. also the experimental part) by partial saponification of the corresponding bisanhydrides, and the monoanhydrides resulting in this case do not have to be isolated.

$N^3$-(2,6-Dioxomorpholinoethyl)-$N^6$-(ethoxycarbonylmethyl)-3,6-diazaoctanedioic acid A suspension of 21.1 g (50 mmol) of $N^3$,$N^6$-bis-(carboxymethyl)-$N^9$-(ethoxy-carbonylmethyl)-3,6,9-triazaundecanedioic acid in 250 ml of acetic anhydride is allowed to stir for three days at room temperature after the addition of 42.2 ml of pyridine. Then, the precipitate is suctioned off, washed three times with 50 ml of acetic anhydride each and then stirred for several hours with absolute diethyl ether. After suctioning off, washing with absolute diethyl ether and drying in a vacuum at 40° C., 18.0 g (=89% of theory) of a white powder with a melting point of 195°–196° C. is obtained.

Analysis (relative to the anhydrous substance): Calculated: C 47.64 H 6.25 N 10.42; Found: C 47.54 H 6.30 N 10.22

The reaction of the acid anhydrides in the amines is performed in the liquid phase. Suitable reaction media are, for example, water, dipolar aprotic solvents such as acetonitrile, N-methylpyrrolidone, dimethylformamide, dimethylacetamide and the like or mixtures of the same. The reaction temperatures are between about 0° C.–100° C., and temperatures of 20° C.–80° C. are preferred. The reaction times are between 0.5 hours and 2 days, preferably between 1 hour and 36 hours.

The production of the esters of general formula II takes place in a known way, e.g., according to the process described in R. A. Guilmette et al., J. Pharm. Sci. 68, 194 (1979).

The aminolysis of the esters takes place in the liquid phase, e.g., in a suitable, higher-boiling solvent, such as dimethylformamide, dimethylacetamide or dimethyl sulfoxide. The reaction temperatures are at about 20° C.–200° C., and temperatures of 100° C.–180° C. are preferred. The reaction times are between 2 hours and 2 days, and reaction times between 4 hours and 36 hours are preferred.

Further, all methods known to one skilled in the art for conversion of carboxyl groups to amide groups for synthesis of the complexing agents of general formula I according to the invention, can be used, thus, e.g., the method according to Krejcarek and Tucker, Biochem. Biophys. Res. Commun. 77, 581 (1977) on mixed anhydrides. Other methods to convert activated carbonyl groups are described, e.g., in J. Nucl. Med. 24, 1158 (1983), Bioconjugate Chem. 1, 65 (1990), Org. Prep. Proc. Int. 7, 215 (1975), Adv. Org. Chem. Part B, 472 and Fieser, Reagents for Organic Syntheses 10, 142 (carbodiimide).

The production of the compounds needed as initial substances for the C-substituted (i.e. one of substituents $Z^1$ and $Z^2$ is not hydrogen) anhydrides or esters of general formulas II and III takes place in that, in a way known in the art, compounds of general formula V

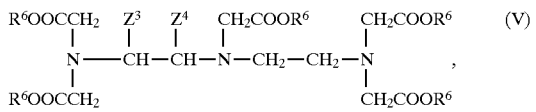

in which

R⁶ stands for an acid protecting group,

Z³ and Z⁴ each stand for a hydrogen atom or the radical —(CH$_2$)$_m$—(C$_6$H$_4$)$_q$—OH, provided that one of substituents Z³ and Z⁴ stands for a hydrogen atom and the other for the indicated radical, are converted to a compound with the radical indicated for Z¹ and Z² and acid protecting groups R⁶ are cleaved.

As acid protecting groups R⁶, lower alkyl, aryl, and aralkyl groups are suitable, for example, the methyl, ethyl, propyl, n-butyl, t-butyl, phenyl, benzyl, diphenylmethyl, triphenylmethyl, bis(p-nitrophenyl)-methyl group as well as trialkylsilyl groups.

The cleavage of protecting groups R⁶ takes place according to the processes known to one skilled in the art [e.g., E. Wuensch, Methoden der Org. Chemie [Methods of Org. Chemistry] (Houben-Weyl), Vol. XV/1, 4th edition 1974, p. 315 ff], for example, by hydrolysis, hydrogenolysis or alkaline saponification of the esters with alkali in aqueous alcoholic solution at temperatures of 0° to 50° C. Organic or inorganic acids are used for cleavage of the t-butylesters especially advantageous for these reactions: the ester compound dissolved in a suitable anhydrous organic solvent, but preferably the pulverized dry substance, is mixed either with hydrogen halide solution in glacial acetic acid, with trifluoroacetic acid or also boron trifluoride diethyl etherate in glacial acetic acid and cleaved at temperatures of –10° C. to 60° C., preferably at room temperature.

The compounds of general formula V being used as feedstocks for the production of the complex compounds according to the invention are known (DOS 3 710 730 and the literature cited there) or can be synthesized analogously to the production instructions described there.

A number of methods known to one skilled in the art from literature are available for the reaction of the known aliphatic or aromatic hydroxy compounds to the corresponding aryl-alkyl ethers or dialkyl ethers (e.g., J. March, Advanced Organic Chemistry, third edition 1985, p. 342 ff).

For this purpose, the compounds of formula V, in which R⁶ stands for an alkali-stable acid protecting group, are dissolved in a polar aprotic solvent, such as, e.g., tetrahydrofuran, dimethoxyethane or dimethyl sulfoxide and mixed with a base, such as, e.g., sodium hydride, sodium hydroxide or alkali carbonates or alkaline-earth carbonates, at temperatures between –30° C. and the boiling point of the respective solvent, but preferably between 0° C. and 60° C.

For this purpose, a compound of general formula VI

Y—(CH$_2$)$_n$—(C$_6$H$_4$)$_r$—(O)$_s$—R  (VI)

is added, in which Y stands for a nucleofuge, such as, e.g., Cl, Br, I, CH$_3$—C$_6$H$_4$SO$_3$ or CF$_3$SO$_3$ and the usual indices have the same meaning as in general formula I.

The reaction times are 30 minutes to 8 hours depending on steric hindrance of the radicals involved.

As an alternative to the above-described reaction conditions, both arylalkyl ether and dialkyl ether can be produced very advantageously by phase transfer catalysis (Starks and Liotta, Phase Transfer Catalysis, Academic Press, N.Y. 1978, pp. 128–138).

For this purpose, the reaction is performed in a two-phase mixture of aqueous base, preferably 30% sodium hydroxide solution, and an organic aprotic solvent which is water-immiscible. As phase transfer catalysts, the compounds known to one skilled in the art are suitable, but preferably tetraalkylammonium or tetraalkylphosphonium salts.

If compounds of general formula I with k, n, l and r=Q and R meaning a hydrogen atom are to be synthesized, it is possible, starting from the corresponding unsubstituted amino acids (e.g., phenylalanine), to perform the synthesis analogously to methods known in the literature.

But if a number of analogous compounds are synthesized, the representation of the phenol derivatives described in DOS 3 710 730 and the reductive removal of the phenol function according to the literature processes known to one skilled in the art are advisable. Above all, the reduction of aryldiethyl phosphates with titanium can be mentioned which can be very advantageously performed also in the presence of ester groups [S. C. Welch et al., J. Org. Chem. 43, 4797–99 (1978) and the literature cited there]. In this case, the corresponding aryldiethyl phosphate is first formed from the phenolic feedstock by reaction with phosphoric acid diethyl ester chloride in 70 to 100% yield, preferably by use of sodium hydride as a base in a polar aprotic solvent. Then the reduction with freshly produced titanium metal is performed. Preferably, anhydrous titanium(III) chloride is reduced by magnesium or potassium in anhydrous tetrahydrofuran under inert gas for the production of highly active titanium.

The above-described diethyl phosphate is added to such a mixture and refluxed for 2 to 24 hours, preferably 6 to 16 hours. After completion of the reaction, it is optionally chromatographically worked up. The palladium-catalyzed reduction of the corresponding aryl triflates is also usable according to S. Cacchi et al., Tetr. Lett. 27, 5541–44 (1986).

The compounds of general formula I, thus obtained finally, with X meaning a hydrogen atom, represent complexing agents. They can be isolated and purified or converted without isolation to metal complexes of general formula I with at least two of substituents X meaning a metal ion equivalent.

The production of the metal complexes according to the invention takes place in the way disclosed in German laid-open specification 34 01 052, by the metal oxide or a metal salt (for example, the nitrate, acetate, carbonate, chloride or sulfate) of the element of atomic numbers 21–29, 42, 44, 57–83 being dissolved or suspended in water and/or a lower alcohol (such as methanol, ethanol or isopropanol) and reacted with the solution or suspension of the equivalent amount of the complexing ligands and then, if desired, present acidic hydrogen atoms being substituted by cations of inorganic and/or organic bases or amino acids.

The neutralization of possibly still present free acid groups takes place with the help of inorganic bases (for example, hydroxides, carbonates or bicarbonates) of, for example, sodium, potassium, lithium, magnesium or calcium and/or organic bases, such as, among others, primary, secondary and tertiary amines, such as, for example, ethanolamine, morpholine, glucamine, N-methylglucamine and N,N-dimethylglucamine, as well as basic amino acids, such as, for example, lysine, arginine and ornithine or of amides of originally neutral or acid amino acids.

For production of neutral complex compounds, for example, of the acid complex salts in aqueous solution or suspension as much as the desired bases can be added, so that the neutral point is reached. The solution obtained can then be evaporated to dryness in a vacuum. It is often advantageous to precipitate the formed neutral salts by adding water-miscible solvents, such as, for example, lower alcohols (methanol, ethanol, isopropanol and others), lower ketones (acetone and others), polar ethers (tetrahydrofuran, dioxane, 1,2-dimethoxyethane and others) and thus easily to obtain crystallizates that can be easily isolated and purified. It has proven especially advantageous to add the desired base already during the complexing of the reaction mixture and thus to save a process step.

If the acid complex compounds contain several free acidic groups, it is often advisable to produce neutral mixed salts which contain both inorganic and organic cations as counterions.

This can happen, for example, by the complexing ligands in aqueous suspension or solution being reacted with the oxide or salt of the element providing the central ion and half of the amount needed for neutralization of an organic base, the formed complex salt being isolated, optionally purified and then, for complete neutralization, being mixed with the necessary amount of an inorganic base. The sequence of addition of the bases can also be reversed.

Another possibility to achieve neutral complex compounds consists in converting the remaining acid groups in the complex completely or partially to, for example, esters or amides. This can happen by later reaction on the finished complex (e.g., by exhaustive reaction of the free carboxy groups with dimethyl sulfate).

The production of the pharmaceutical agents according to the invention also takes place in a way known in the art, by the complex compounds according to the invention—optionally by adding the additives usual in galenicals—being suspended or dissolved in an aqueous medium and then the suspension or solution optionally being sterilized. Suitable additives are, for example, physiologically harmless buffers (such as, for example, tromethamine), additives of complexing agents (such as, for example, diethylenetriaminepentaacetic acid) or—if necessary—electrolytes, such as, for example, sodium chloride or—if necessary—antioxidants, such as, for example, ascorbic acid.

If suspensions or solutions of the agents according to the invention in water or physiological salt solution are desired for the enteral administration or other purposes, they are mixed with one or more auxiliary agent(s) (for example, methyl cellulose, lactose, mannitol) and/or surfactant(s) (for example, lecithins, Tween®, Myrj° and/or aromatic substance(s) for taste correction (for example, ethereal oils) which are usual in galenicals.

On principle, it is also possible to produce the pharmaceutical agents according to the invention even without isolating the complex salts. In each case, special care then has to be used to carry out the chelate formation so that the salts and salt solutions according to the invention are practically free of noncomplexed, toxically acting metal ions.

This can be assured, for example, with the help of color indicators such as xylenol orange by control filtrations during the production process. The invention therefore also relates to processes for the production of complex compounds and their salts. A purification of the isolated complex salt remains as a final safety measure.

The pharmaceutical agents according to the invention preferably contain 0.1 micromol–1 mol/l of complex salt and are generally dosed in amounts of 0.1 micromol–5 mmol/kg. They are intended for enteral and parenteral administration. The complex compounds according to the invention are used 1. for the NMR and X-ray diagnosis in the form of their complexes with the ions of the elements with atomic numbers 21–29, 42, 44 and 57–83;
2. for the radiodiagnosis and the radiotherapy in the form of their complexes with the radioisotopes of the elements with atomic numbers 21, 27, 29, 31, 32, 37–40, 43, 49, 62–64, 70, 75 and 77.

The agents according to the invention meet the varied requirements for suitability as contrast media for the nuclear spin tomography. Thus, they are excellently suited for this purpose, after oral or parenteral administration, to improve the image, obtained with the help of the nuclear spin tomography, in its expressiveness by increasing the signal intensity. Further, they show the high effectiveness which is necessary to load the body with the smallest possible amounts of foreign substances, and the good compatibility which is necessary to maintain the noninvasive nature of the tests.

The good water solubility and low osmolality of the agents according to the invention make it possible to produce highly concentrated solutions, thus to keep the volume load of the circulatory system within justifiable limits and to offset the dilution by the body fluid, i.e., NMR diagnostic agents have to be 100 to 1000 times more water-soluble than for the NMR spectroscopy. Further, the agents according to the invention exhibit not only a high stability in vitro but also a surprisingly high stability in vivo, so that a release or an exchange of the ions—toxic in themselves—noncovalently bound in the complexes takes place only extremely slowly within the time in which the new contrast media are again completely excreted.

In general, the agents according to the invention for use as NMR diagnostic agents are dosed in amounts of 0.0001–5 mmol/kg of body weight, preferably 0.005–0.5 mmol/kg of body weight of the complex according to the invention. Aqueous formulations of the concentration of 50 micromol/l to 2 mol/l, preferably 100 mmol/l to 1 mol/l, are used in an intravenous injection. A rectal as well as an oral use is preferably performed with solutions of the concentration 0.1 mmol to 100 mmol/l or as solid in the corresponding concentration range. The volumes administered are between 5 ml and 2 l depending on the diagnostic formulation of the problem. Details of the use are discussed, for example, in H. J. Weinmann et al., Am. J. of Roentgenology 142, 619 (1984).

Especially low dosages (less than 1 mg/kg of body weight) of organ-specific NMR diagnostic agents can be used, for example, for detection of tumors and myocardial infarctions.

Further, the complex compounds according to the invention can be used advantageously as susceptibility reagents and as shift reagents for the in vivo NMR spectroscopy.

The agents according to the invention are suitable also as radiodiagnostic agents because of their advantageous radioactive properties and the good stability of the complex compounds contained in them. Details of their use and dosage are described, e.g., in "Radiotracers for Medical Applications," CRC Press, Boca Raton, Fla.

Another imaging method with radioisotopes is the positron emission tomography, which uses positron-emitting isotopes, such as, e.g. $^{43}$Sc, $^{44}$Sc, $^{52}$Fe, $^{55}$Co and $^{68}$Ga (Heiss, W. D.; Phelps, M. E.; Positron Emission Tomography of Brain, Springer Verlag Berlin, Heidelberg, New York 1983).

The compounds according to the invention can also be used in radio-immunotherapy or radiation therapy. These are distinguished from the corresponding diagnostic agents only by the amount and type of the isotope used. In this case, the purpose is the destruction of the tumor cells by high-energy shortwave radiation with a smallest possible range of action. Suitable beta-emitting ions are, for example, $^{46}$Sc, $^{47}$Sc, $^{48}$Sc, $^{72}$Ga, $^{73}$Ga and $^{90}$Y. Suitable alpha-emitting ions exhibiting small half-lives are, for example, $^{211}$Bi, $^{212}$Bi, $^{213}$Bi and $^{214}$Bi, and $^{212}$Bi is preferred. A suitable photon- and electron-emitting ion is $^{158}$Gd, which can be obtained from $^{157}$Gd by neutron capture.

If the agent according to the invention is intended for use in the variant of the radiation therapy proposed by R. L. Mills et al. [Nature Vol. 336, (1988), p. 787], the central ion has to be derived from a Moessbauer isotope, such as, for example, $^{57}$Fe or $^{151}$Eu.

In the in vivo administration of the therapeutic agents according to the invention, the latter can be administered together with a suitable vehicle, such as, for example, serum or physiological common salt solution and/or together with another protein, such as, for example, human serum albumin. The dosage in this case is dependent on the type of cellular impairment, the metal ion used and the type of method, e.g., brachytherapy.

The therapeutic agents according to the invention are administered parenterally, preferably i.v.

Details of the use of radiotherapeutic agents are discussed, e.g., in R. W. Kozak et al. TIBTEC, October 1986, 262.

The agents according to the invention are excellently suited as X-ray contrast media, and it is to be emphasized especially that with them, no signs of the anaphylactic-type reactions, known from the iodine-containing contrast media, can be discerned in biochemical-pharmacological tests. They are especially valuable because of the advantageous absorption properties in the areas of higher tube voltages for digital substraction techniques.

In general, the agents according to the invention for use as X-ray contrast media are dosed analogously to, for example, meglumine-diatrizoate in amounts of 0.1–5 mmol/kg, preferably 0.25–1 mmol/kg.

Details of the use of X-ray contrast media are discussed, for example, in Barke, Roentgenkontrastmittel [X-Ray Contrast Media], G. Thieme, Leipzig (1970) and P. Thurn, E. Buecheler—"Einfuehrung in die Roentgendiagnostik" [Introduction to the X-Ray Diagnosis], G. Thieme, Stuttgart, N.Y. (1977).

Altogether, it has been possible to synthesize new complexing agents, metal complexes and metal complex salts, which open up new possibilities in diagnostic and therapeutic medicine. Above all, the development of novel imaging processes in medical diagnosis makes this development appear desirable.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 40 11 684.0, are hereby incorporated by reference.

EXAMPLES

Figure 1:
FIG. 1 is an MRI image of a test animal (rat) made without the administration of contrast media.
Figure 2:
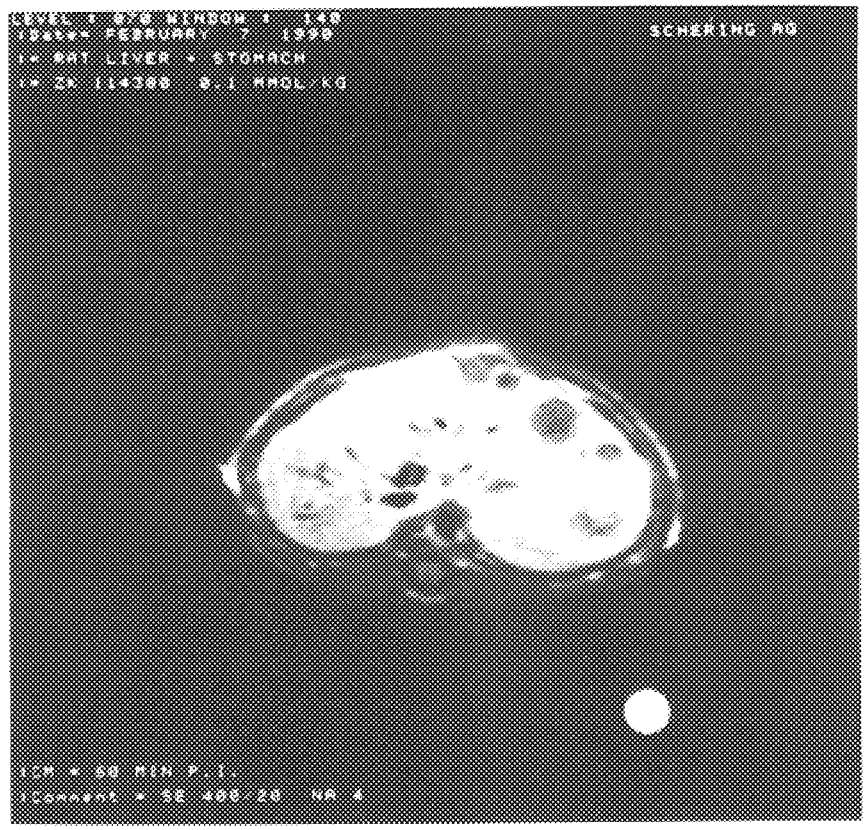
FIG. 2 is an MRI image of a test animal (rat) taken 60 minutes after the administration of cantrast medium (Example 1b).
Figure 3:
FIG. 3 is an MRI image of a test animal (rat) taken 45 minutes after the administration of contrast medium (Example 1b).
Figure 4:
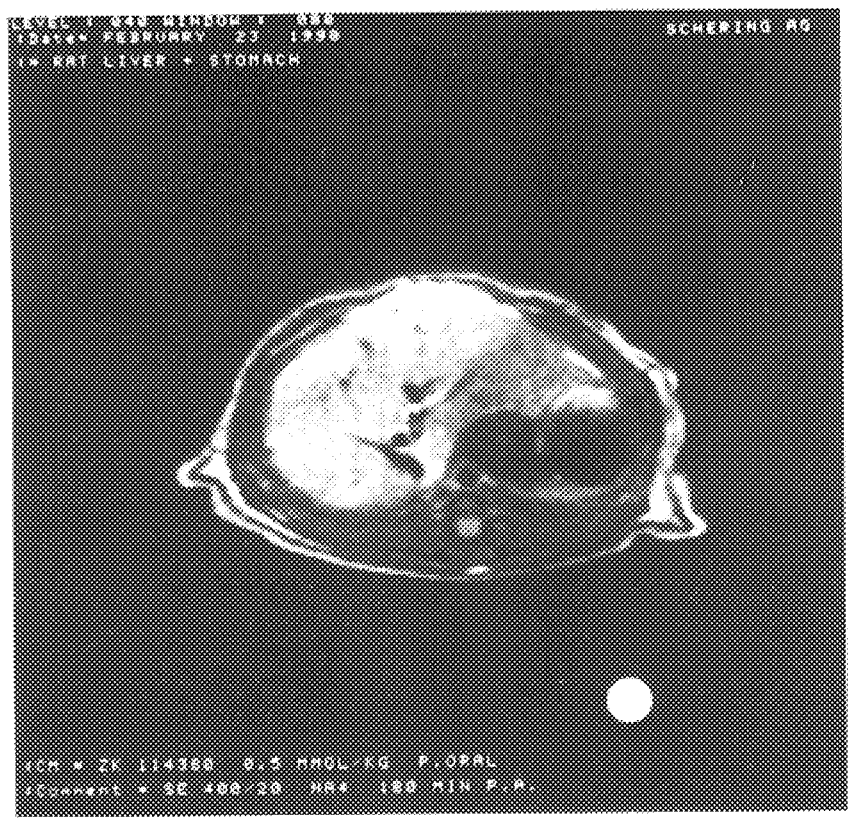
FIG. 4 is an MRI image of a test animal (rat) taken 180 minutes after the administration of contrast medium (Example 1b).

Example 1 a) 3,6-Bis(carboxymethyl)-9-(10-carboxydecylcarbamoylmethyl)-3,6,9-triazaundecanedioic acid 15.33 g (38 mmol) of $N^3$-(2,6-dioxomorpholinoethyl)-$N^6$-(ethoxy-carbonylmethyl)-3,6-diazaoctanedioic acid (Example 13a of EP 0331 616) is suspended in dimethylformamide (DMF) and mixed in an ice bath with 21.07 ml (152 mmol) of triethylamine and 7.65 g (38 mmol) of 11-aminoundecanoic acid. The temperature is allowed to increase to room temperature and the reaction solution is stirred overnight. After completion of the reaction, the possibly still slightly cloudy solution is filtered and the filtrate is concentrated by evaporation in a vacuum. The residue is absorptively precipitated with ether and then recrystallized from water (17.8 g). The ethyl ester is dissolved in 2 N NaOH and is adjusted to pH 7 after 3 hours by adding Amberlite® IR 120 ($H^+$). The ion exchange material is suctioned off, the filtrate is freeze-dried (20.1 g) and then added to $H_2O$/methanol (2:1) on 100 ml of Amberlite° IR 120 ($H^+$) and the acid eluate is concentrated by evaporation and recrystallized from water.

Yield: 13.0 g (59.3%); Melting point: 168° C.; Analysis (relative to the anhydrous substance): Calculated: C 52.07 H 7.69 N 9.72; C 51.98 H 7.61 N 9.75 b) Gadolinium complex of 3,6-bis(carboxymethyl)-9-(10-carboxydecylcarbamoylmethyl)-3,6,9-triazaundecanedioic acid 8.65 g (15 mmol) of the complexing agent acid described in Example 1a is suspended in 200 ml of $H_2O$ and mixed with 2.72 g (7.5 mmol) of $Gd_2O_3$ and held at 90° C. for 60 minutes on the water bath. The solution is filtered by a membrane filter, frozen and freeze-dried.

Yield: 11.9 g (quantitative); $H_2O$ content: 9.2% (Karl-Fischer); Analysis (relative to the anhydrous substance): Calculated: C 41.08 H 5.65 Gd 21.52 N 7.67; C 41.12 H 5.69 Gd 21.37 N 7.59 c) Europium complex of 3,6-bis(carboxymethyl)-9-(10)-carboxydecylcarbamoylmethyl)-3,6,9-triazaundecanedioic acid Analogously, the title compound is obtained as a white powder with an uncharacteristic decomposition point from the complexing agent acid, described in Example 1a, with europium oxide, $Eu_2O_3$, in quantitative yield.

Analysis (relative to the anhydrous substance): Calculated: C 40.52 H 5.58 N 7.56 Eu 22.58; C 40.60 H 5.65 N 7.63 Eu 22.51 d) Iron(III) complex of 3,6-bis-(carboxymethyl)-9-(10-carboxydecylcarbamoylmethyl)-3,6,9-triazaundecanedioic acid Analogously, the title compound is obtained as a brown powder with an uncharacteristic decomposition point from the complexing agent acid, described in Example 1a, with iron(III) oxide, $Fe_2O_3$, in quantitative yield.

Analysis (relative to the anhydrous substance): Calculated: C 63.19 H 9.33 N 11.79 Fe 11.75; C 63.04 H 9.42 N 11.68 Fe 11.79 e) Bismuth(III) complex of 3,6-bis-(carboxymethyl)-9-(10-carboxydecylcarbamoylmethyl)-3,6,9-triazaundecanedioic acid Analogously, the title compound is obtained as a brown power with an uncharacteristic decomposition point from the complexing agent acid, described in Example 1a, with bismuth(III)oxide, $Bi_2O_3$, in quantitative yield.

Analysis (relative to the anhydrous substance): Calculated: C 47.79 H 7.06 N 8.92 Bi 33.26; C 47.83 H 7.11 B 8.88 Bi 33.10

Example 2 a) 6-Carboxymethyl-9-(4-carboxymethyl-phenyl)-carbamoylmethyl-3-ethoxycarbonylmethyl-3,6,9-triazaundecanedioic acid 3.02 g (20 mmol) of p-aminophenylacetic acid is added to a suspension of 8.07 g (20 mmol) of $N^3$-(2,6-dioxomorpholinoethyl)-$N^6$- (ethoxy-carbonylmethyl)-3,6-diazaoctanedioic acid in 100 ml of dimethylformamide at 45° C. with stirring, then stirred overnight at room temperature, the solvent is largely evaporated in a vacuum and the residue is stirred with 100 ml of methyl tert-butyl ether, suctioned off and the residue is dried in a vacuum at 50° C. The crude product thus obtained is suspended with 10 ml of water. It is mixed with 11 N sodium hydroxide solution up to pH 7, and the substance goes into solution. 10 g of silica gel is added to the solution, the suspension is concentrated by evaporation in a rotary evaporator and the residue is added to a column with 700 g of silica gel, which was taken up with a mixture of chloroform-methanol-glacial acetic acid-water (18-10-4-4). It is eluted with the same solvent and, after concentration by evaporation of the eluate, 8.3 g of oily product is isolated that is dissolved in 75 ml water for removal of sodium ions and is added to a column of 75 ml of cation exchanger IR 120. The column is eluted with 150 ml of water and the aqueous solution is concentrated by evaporation in a vacuum. The residue is stirred with 50 ml of diethyl ether, suctioned off, dried in a vacuum, and 6.2 g of the title compound is obtained as a white powder.

Analysis (relative to the anhydrous substance): Calculated: C 51.98 H 6.18 N 10.10; C 51.81 H 6.33 N 10.18 b) 3,6-Bis(carboxymethyl)-9-(4-carboxymethylphenyl)-carbamoylmethyl-3,6,9-triazaundecanedioic acid 90 ml of 1N sodium hydroxide solution is added to a solution of 5 g of the ester, produced according to part a), in 20 ml of water, allowed to stand for 3 hours at room temperature and about 200 ml of cation exchanger IR 120 is added to the solution with stirring, the solution then has a pH of 2.3. After filtration, the solution is freeze-dried. 3.90 g of the title compound is obtained as a white powder.

Analysis (relative to the anhydrous substance): Calculated: C 50.19 H 5.74 N 10.64; C 50.03 H 5.71 N 10.72 c) Gadolinium complex of 3,6-bis(carboxymethyl)-9-(4-carboxymethyl-phenyl)-carbamoylmethyl-3,6,9-triazaundecanedioic acid 1.053 g (2 mmol) of the substance produced according to part b) is heated in 50 ml of water with 362 mg (1 mmol) of gadolinium oxide for 1 hour to 80°–85° C. In this case, the oxide goes into solution. It is filtered by a 0.1 micron membrane filter and the substance is isolated by freeze-drying. 1.35 g of the title compound is obtained as a white powder.

Analysis (relative to the anhydrous substance): Calculated: C 38.82 H 4.00 Gd 23.10 N 8.23; C 38.57 H 4.40 Gd 22.95 N 8.33

Example 3 a) 6-Carboxymethyl-9-[4-(carboxyisopropyl)-phenyl]-carbamoylmethyl-3-ethoxycarbonylmethyl-3,6,9-triazaundecanedioic acid Analogously to Example 2a, the title compound is obtained from $N^3$-(2,6-dioxomorpholinoethyl)-$N^6$-(ethoxycarbonylmethyl)-3,6-diazaoctanedioic acid and alpha,alpha-dimethyl-p-aminophenylacetic acid.

Analysis (relative to the anhydrous substance): Calculated: C 53.60 H 6.57 N 6.92; C 53.44 H 6.88 N 9.49 b) 3,6-Bis(carboxymethyl)-9-[4-(carboxyisopropyl)-phenyl]-carbamoylmethyl-3,6,9-triazaundecanedioic acid Analogously to Example 2b, the title compound is obtained by alkaline saponification of 6-carboxymethyl-9-[4-(carboxyisopropyl)-phenyl]-carbamoylmethyl-3-ethoxycarbonylmethyl-3,6,9-triazaundecanedioic acid.

Analysis (relative to the anhydrous substance): Calculated: C 51.98 H 6.18 N 10.10; C 51.79 H 6.35 N 10.01 c) Gadolinium complex of 3,6-bis(carboxymethyl)-9-[4-(carboxyisopropyl)-phenyl]-carbamoylmethyl-3,6,9-triazaundecanedioic acid Analogously to Example 2c, the title compound is obtained by complexing of the ligand with gadolinium oxide.

Analysis (relative to the anhydrous substance): Calculated: C 40.67 H 4.41 Gd 22.19 N 7.90; C 40.47 H 4.60 Gd 22.01 N 7.80

Example 4 a) 3,6-Bis(carboxymethyl)-9-(11-carboxy-1-n-hexyl-undecylcarbamoylmethyl)-3,6,9-triazaundecanedioic acid 15.33 g (38 mmol) of $N^3$-(2,6-dioxomorpholinoethyl)-$N^6$-(ethoxycarbonylmethyl)-3,6-diazaoctanedioic acid (Example 13a of EP 0 331 616) is suspended in 100 ml of dimethylformamide and mixed in an ice bath with 21.07 ml (152 mmol) of triethylamine and 11.36 g (38 mmol) of 12-aminooctadecanoic acid. After stirring overnight at room temperature, it is concentrated by evaporation in a vacuum, and the residue is absorptively precipitated with 500 ml of diethyl ether. It is suctioned off and the dried reaction product is dissolved in 50 ml of 2 n sodium hydroxide solution. After three hours of stirring, it is neutralized with dilute hydrochloric acid, evaporated to dryness in a vacuum and recrystallized from water. 15.64 g (61% of theory) of a gray powder is obtained.

Analysis (relative to the anhydrous substance): Calculated: C 56.95 H 8.66 N 8.30; C 56.87 H 8.77 N 8.35 b) Gadolinium complex of 3,6-bis(carboxymethyl)-9-(11-carboxy-1-n-hexyl-undecylcarbamoylmethyl)-3,6,9-triazaundecanedioic acid 10.12 g (15 mmol) of the above-described compound is suspended in 200 ml of water and mixed with 2.72 g (7.5 mmol) of gadolinium oxide. It is heated for 60 minutes to 90° C., allowed to cool off to room temperature, filtered, and the solution is freeze-dried. 12.43 g (quantitative) of the title compound is obtained as a white powder.

Analysis (relative to the anhydrous substance): Calculated: C 46.36 H 6.69 N 6.76 Gd 18.97; C 46.31 H 6.75 N 6.68 Gd 18.95

The substance forms associates in aqueous solution with human serum albumin.

Example 5 a) 3,6-Bis(carboxymethyl)-9-(10-carbethoxydecylcarbamoylmethyl)-3,6,9-triazaundecanedioic acid 17.85 g (50 mmol) of 1.5-bis(2,6-dioxomorpholino)-3-carboxymethyl-3-azapentane is stirred in 200 ml of dimethylformamide and mixed with 9 ml (50 mmol) of water. The solution is heated for 3 hours to 70° C., cooled off to 0° C. and 36.07 ml (260 mmol) of triethylamine and 10.8 g (50 mmol) of 11-aminoundecanoic acid ethyl ester are added. After stirring overnight at room temperature, the solution is evaporated to dryness in a vacuum. The residue is taken up in 100 ml of water and the solution is mixed by drops with concentrated hydrochloric acid until permanent cloudiness. After stirring overnight in the ice bath, the finely crystalline precipitate is suctioned off, washed with water and dried in a vacuum at 50° C. 14.9 g (65% of theory) of the title compound is obtained as a white powder with melting point 155°–157° C.

Analysis (relative to the anhydrous substance): Calculated: C 53.63 H 8.00 N 9.27; C 53.58 H 8.22 N 9.41 b) Gadolinium complex of 3,6-bis(carboxymethyl)-9-(10-carbethoxydecylcarbamoylmethyl)-3,6,9-triazaundecanedioic acid 9.08 g (15 mmol) of the compound described in Example 5a) is suspended in 200 ml of water, mixed with 2.72 g (7.5 mmol) of $Gd_2O_3$ and brought to clear solution with stirring at room temperature. By freeze-drying, the gadolinium complex is obtained as white powder in quantitative yield.

Analysis (relative to the anhydrous substance): Calculated: C 42.73 H 5.98 N 7.38 Gd 20.72; C 42.80 H 5.87 N 7.51 Gd 20.63

Example 6 a) 1,5-Bis(2,6-dioxomorpholino)-2-(4-ethoxybenzyl)-3-carboxymethyl-3-azapentane 52.8 g (100 mmol) of 3,6,9-triaza-3,6,9-tris(carboxymethyl)-4-(4-ethoxybenzyl)undecanedioic acid, produced according to EP publication no. 0 405 704 [Example 8b)], is suspended in 75 ml of acetic anhydride. 38 ml of pyridine is added and heated for 3 hours to 50° C. After cooling off to room temperature and stirring overnight, the precipitate is suctioned off, washed three times with 200 ml of diethyl ether each and dried in a vacuum at 30° C. 40.3 g (82% of theory) of the title compound is obtained as a white powder with melting point 172°–174° C.

Analysis Calculated: C 56.21 H 5.95 N 8.55; C 56.35 H 5.88 N 8.60 b) 3,6-Bis(carboxymethyl)-4-(4-ethoxybenzyl-9-(10-carboxydecylcarbamoylmethyl)-3,6,9-triazaundecanedioic acid and 6,9-bis(carboxymethyl)-4-(4-ethoxybenzyl-3-(10-carboxydecylcarbamoylmethyl)-3,6,9-triazaundecanedioic acid 24.6 g (50 mmol) of the compound obtained according to Example 6a) is stirred in 200 ml of dimethylformamide and mixed with 9 ml (50 mmol) of water. The solution is heated for 3 hours to 70° C., cooled off to 0° C. and 36.07 ml (260 mmol) of triethylamine and 10.0 g (50 mmol) of 11-aminoundecanoic acid are added. After stirring overnight at room temperature, the solution is evaporated to dryness in a vacuum. The residue is taken up in 500 ml of water and mixed by instillation with concentrated hydrochloric acid until permanent cloudiness. After stirring overnight in the ice bath, the precipitate is suctioned off, washed with water and dried in a vacuum at 50° C. 21.3 g (60% of theory) of the isomer mixture is obtained as a white powder with melting point 184°–186° C.

Analysis (relative to the anhydrous substance): Calculated: C 57.45 H 7.66 N 7.88; C 57.38 H 7.80 N 7.95 c) Gadolinium complex of 3,6-bis(carboxymethyl)-4-(4-ethoxybenzyl)-9-(10-carboxydecylcarbamoylmethyl)-3,6,9-triazaundecanedioic acid and 6,9-bis(carboxymethyl)-4-(4-ethoxybenzyl)-3-(10-carboxydecylcarbamoylmethyl)-3,6,9-triazaundecanedioic acid 10.65 g (15 mol) of the complexing agent described in Example 6b) is suspended in 200 ml. of water and mixed with 2.72 g (7.5 mmol) of $Gd_2O_3$. It is heated for 1 hour to 90° C., the solution is added by a membrane filter and the complexes are isolated as a white powder by freeze-drying in quantitative yield.

Analysis (relative to the anhydrous substance): Calculated: C 47.20 H 5.94 N 6.48 Gd 18.18; C 47.15 H 5.73 N 6.39 Gd 18.30

Example 7 a) 3,6,9-tris-Carboxymethyl-3,6,9-triazaundecanedioic acid-[N-methyl-N'-(4-carboxyphenyl)]monoamide 15.33 g (38 mmol) of $N^3$-(2,6-dioxomorpholinoethyl)-$N^6$-(ethoxycarbonylmethyl)-3,6-diazaoctanedioic acid [Example 13a] of EP 0 331 616] is suspended in 100 ml of dimethylformamide and mixed at 0° C. with 21 ml of triethylamine and 5.74 g (38 mmol) of 4-N-methylaminobenzoic acid. After stirring overnight at room temperature, it is evaporated to dryness in a vacuum, and the residue is absorptively precipitated with 500 ml of diethyl ether. It is suctioned off and, after recrystallization from ethanol, 11.9 g (60% of theory) of the title compound is obtained as a white powder.

Analysis Calculated: C 50.28 H 5.56 N 10.66; C 50.35 H 5.61 N 10.58 b) Gadolinium complex of 3,6,9-tris-carboxymethyl-3,6,9-triazaundecanedioic acid [N-methyl-N'-(4-carboxyphenyl]monoamide 7.88 g (15 mmol) of the above-described compound is suspended in 200 ml of water and mixed with 2.72 g (7.5 mmol) of $Gd_2O_3$. It is heated for 60 minutes to 90° C., allowed to cool off to room temperature and the solution is freeze-dried. The title compound is obtained as a white powder with an uncharacteristic decomposition point in quantitative yield.

Analysis (relative to the anhydrous substance): Calculated: C 38.87 H 3.86 N 8.24 Gd 23.13; C 38.81 H 3.94 N 8.31 Gd 23.25

Examples for the Form of Administration

Production of a solution of the gadolinium complex of 3,6-bis(carboxymethyl)-9-(10-carboxydecylcarbamoylmethyl)-3,6,9-triazaundecanedioic acid 365.43 g (0.5 mol) of the compound described in Example 1b is dissolved with adding 195.22 g (1 mol) of N-methylglucamine in 600 ml of water per injection (p.i.). After adding 3.22 g of monohydrate of the calcium trisodium salt of the DTPA, $CaNa_3$ DTPA and 1.21 g of trishydroxymethylaminomethane are adjusted with dilute hydrochloric acid to pH 7.0 and filled up with water p.i. to 1000 ml. The solution is ultrafiltered, bottled in flasks and heat-sterilized.

Composition of a Powder for Oral Administration 12.8 g (35 mmol) of the compound described in Example 1b; 12.0 g of sucrose; 0.5 g of polyoxyethylenepolyoxypropylene polymer; 0.001 g of aromatic substances Example for an In Vivo NMR Diagnosis A cell suspension of the Brown-Pearce tumor was injected in the liver in a test animal (rat, strain lew/mol, female, 155 g) two weeks before the test. In the method used, about 2 weeks were required until the tumor had reached the size of 0.5–1 cm³ desired for the test.

For the test, the animal was anesthetized (Rompun+ Ketavet) and then a catheter was placed in the caudal vein for the administration of the contrast medium.

The imaging took place in an MRI experimental device of the General Electric company (field strength 2 teslas). The first image was made without contrast media with a $T_1$-weighted spin echo sequence (TR=400 msec, TE=20 msec, layer thickness 3 mm). The liver appears with the expected (normal) signal intensity; the tumor is isodense and cannot be defined. Then, the administration of the contrast medium [gadolinium complex of 3,6-bis(carboxymethyl)-9-(10-carboxydecylcarbamoylmethyl)-3,6,9-triazaundecanedioic acid, Example 1b)] took place through the vein catheter with a dose of 0.1 mmol of Gd/kg (concentration of the solution of 0.05 mmol/ml in 0.9% NaCl, i.e. a clinically usual dose, e.g., in the case of the commercial preparation Magnevist®). Image no. 2 was taken 60 minutes after the administration of the contrast medium under conditions which were otherwise the same as image no. 1. The liver parenchyma now appears very bright and the tumor, which is considerably darker in comparison with the surrounding liver tissue, can be discerned clearly. This means that the contrast medium is concentrated in the liver to a great extent, but, not in the tumor. In this respect, a considerable advantage is offered here for the diagnosis of liver tumors relative to the previous single contrast medium Magnevist®, found on the market, for the nuclear spin tomography.

Based on the very strong enhancement of the stomach in image no. 2, it is further shown that the substance is obviously also secreted in the stomach. This offers further diagnostic possibilities with respect to a better differentiation of liver and stomach.

In another animal (rat, strain Lew/mol, female, 200 g), the same contrast medium was administered orally with a p.o. sample in a dose of 0.5 mmol of Gd/kg (concentration of the solution 0.033 mmol of Gd/ml, in 0.9% NaCl). The animal was anesthetized 30 minutes after the administration and examined under the same conditions as described in the first case. As early as 45 minutes (image 3) after the administration, a slight increase in the signal in the liver becomes apparent. A marked enhancement in the liver can be discerned 180 minutes after administration (image 4) which suggests that the substance is resorbed in the small intestine after oral administration and is immediately taken up again for the most part by the liver. This finding agrees very well with the pharmacokinetic data. Thus it follows that a liver tumor diagnosis is possible also with an oral administration of the contrast medium.

KEY:
Bild 1=Image 1
Bild 2=Image 2
Bild 3=Image 3
Bild 4=Image 4

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method of NMR imaging comprising imaging a patient to whom a contrast agent has been administered, the improvement wherein said contrast agent is a physiologically acceptable chelate compound of formula I

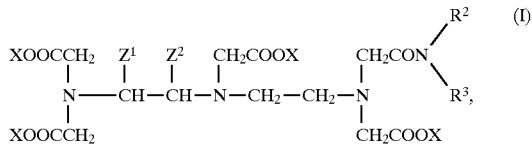

wherein $Z^1$ and $Z^2$ are each, independently, H or
—$(CH_2)_m$—$(C_6H_4)_q$—$(O)_k$—$(CH_2)_n$—$(C_6H_4)_l$—$(O)_r$—R, m and n are each independently 0–20, k, l, q and r are each independently 0 or 1, and R is H, $C_1$–$C_6$-alkyl, $C_1$–$C_6$-alkyl substituted by $OR^1$, or $CH_2COOR^1$, $R^1$ is H, $C_1$–$C_6$-alkyl, or benzyl, $R^2$ is a saturated, unsaturated, straight-chain or branched-chain or cyclic non-aromatic hydrocarbyl group with up to 20 C-atoms which is substituted by a carboxyl group, a sulfone group, a carboxyl group esterified with $C_1$–$C_6$-alkyl or benzyl, or a sulfone group esterified with $C_1$–$C_6$-alkyl or benzyl, an aryl group of up to 10 C-atoms substituted by a carboxyl group, a sulfone group, a carboxyl group esterified with $C_1$–$C_6$-alkyl or benzyl or a sulfone group esterified with $C_1$–$C_6$-alkyl or benzyl, or an aralkyl group of up to 16 C-atoms substituted by a carboxyl group, a sulfone group, a carboxyl group esterified with $C_1$–$C_6$-alkyl or benzyl, or a sulfone group esterified with $C_1$–$C_6$-alkyl or benzyl, $R^3$ is H or a saturated, unsaturated, straight-chain or branched-chain or cyclic non-aromatic hydrocarbyl group with up to 20 C-atoms, which is optionally substituted by a carboxyl group, a sulfone group, a carboxyl group esterified with $C_1$–$C_6$-alkyl or benzyl, or a sulfone group esterified with $C_1$–$C_6$-alkyl or benzyl, an aryl group of up to 10 C-atoms which is optionally substituted by a carboxyl group, a sulfone group, a carboxyl group esterified with $C_1$–$C_6$-alkyl or benzyl, or a sulfone group esterified with $C_1$–$C_6$-alkyl or benzyl, or an aralkyl group of up to 16 C-atoms optionally substituted by a carboxyl group, a sulfone group, a carboxyl group esterified with $C_1$–$C_6$-alkyl or benzyl, or a sulfone group esterified with $C_1$–$C_6$-alkyl or benzyl, X is H and/or a metal ion equivalent of an element of atomic numbers 21–29, 31, 32, 37–40, 42–44, 49 or 57–83, wherein acid groups are, in each case, optionally present as an ester with $C_1$–$C_6$-alkyl, benzyl or 4-methoxybenzyl, or as an amide wherein the nitrogen atom of said amide is substituted by at least one saturated or unsaturated straight-chain, branched-chain or cyclic hydrocarbon radical with up to 5 C atoms, wherein said at least one hydrocarbon radical is optionally substituted by 1–3 hydroxy groups and/or 1–3 $C_1$–$C_4$-hydroxy groups, or said amide is in the form of a 5- or 6-membered heterocyclic ring with inclusion of the amide nitrogen atom; or a salt thereof with an inorganic and/or organic base, an amino acid or an amino acid amide, wherein at least two of substituents X are metal ion equivalents of at least one element of atomic numbers 21–29, 42, 44 or 58–70, at least one of substituents $Z^1$ and $Z^2$ is H, and, if n and l are each 0, then k and r are not both 1.

2. A method according to claim 1, wherein $Z^1$ and $Z^2$ each stand for a hydrogen.

3. A method according to claim 1, wherein $Z^1$ stands for a hydrogen atom and $Z^2$ stands for the radical —$(CH_2)_m$—$(C_6H_4)_q$—$(O)_k$—$(CH_2)_n$—$(C_6H_4)_l$—$(O)_r$—R.

4. A method according to claim 1, wherein $Z^2$ stands for a hydrogen atom and $Z^1$ stands for the radical —$(CH_2)_m$—$(C_6H_4)_q$—$(O)_k$—$(CH_2)_n$—$(C_6H_4)_l$—$(O)_r$—R.

5. A method according to claim 1, wherein $Z^1$ or $Z^2$ stand for the radicals —$CH_2$—$C_6H_4$—OH, —$CH_2$—$C_6H_4$—$OCH_3$, —$CH_2C_6H_5$, —$CH_2$—$C_6H_4$—O—$CH_2$—$C_6H_4$—$OCH_3$, —$CH_2$—O—$CH_2$—$C_6H_5$, —$CH_2$—$C_6H_4$—O—$CH_2$—COOH, —$CH_2$—$C_6H_4$—$OC_2H_5$, —$CH_2$—$C_6H_4$—$OC_4H_9$, —$CH_2$—$C_6H_4$—O—$CH_2$—$C_6H_5$.

6. A method according to claim 1, wherein $R^3$ stands for the methyl, ethyl, propyl, isopropyl, butyl, pentyl, hexyl, phenyl, benzyl, 4-carboxy-phenylene, 1-cyclohexyl-1-carboxylic acid, 1-cyclopentyl-1-carboxylic acid, 2-carboxy-phenylene, 11-carboxy-1-undecyl, 10-carboxy-1-decyl, 7-carboxy-1-heptyl, 6-carboxy-1-hexyl, 5-carboxy-1-pentyl, 4-carboxy-benzyl, 4-carboxy-1-cyclohexylmethyl, 4-carboxymethyl-phenylene, 4-(1,1-dimethylcarboxymethylene)-phenylene, 4-sulfophenylene, 10-sulfo-1-decyl, 8-sulfo-1-octyl, 17-carboxy-7-heptadecyl, 7-carboxy-2-heptyl, 1-carboxy-4-phenyl-2-propyl, 2-carboxyethyl, 4-carboxy-4-but-1-enyl radical.

7. A method according to claim 1, wherein the patient's gastrointestinal tract, renal system and/or hepatobiliary system is imaged.

8. A compound according to claim 1, wherein one COOX group is present as an amide.

9. A method according to claim 1, wherein said compound is a gadolinium complex of 3,6-bis(carboxymethyl)-9-(10-carboxydecylcarbamoylmethyl)-3,6,9-triazaundecanedioic acid.

10. A method according to claim 9, wherein a portion of the patient's hepatobiliary system is imaged.

11. A method of X-ray imaging comprising imaging a patient to whom a contrast agent has been administered, the improvement wherein said contrast agent is a physiologically acceptable chelate compound of formula I $$\begin{array}{c} XOOCCH_2 \quad Z^1 \quad Z^2 \quad CH_2COOX \quad CH_2CON{<}^{R^2}_{R^3} \\ | \quad\quad | \quad | \quad | \quad\quad\quad | \\ N{-}{-}CH{-}CH{-}N{-}CH_2{-}CH_2{-}N \\ | \quad\quad\quad\quad\quad\quad\quad\quad\quad\quad | \\ XOOCCH_2 \quad\quad\quad\quad\quad\quad CH_2COOX \end{array} \quad (I)$$

wherein $Z^1$ and $Z^2$ are each independently H or —$(CH_2)_m$—$(C_6H_4)_q$—$(O)_k$—$(CH_2)_n$—$(C_6H_4)_l$—$(O)_r$—R, m and n are each independently 0–20, k, l, q and r are each independently 0 or 1, and R is H, $C_1$–$C_6$-alkyl, $C_1$–$C_6$-alkyl substituted by $OR^1$, or $CH_2COOR^1$, $R^1$ is H, $C_1$–$C_6$-alkyl, or benzyl, $R^2$ is a saturated, unsaturated, straight-chain or branched-chain or cyclic non-aromatic hydrocarbyl group with up to 20 C-atoms which is substituted by a carboxyl group, a sulfone group, a carboxyl group esterified with $C_1$–$C_6$-alkyl or benzyl, or a sulfone group esterified with $C_1$–$C_6$-alkyl or benzyl, an aryl group of up to 10 C-atoms substituted by a carboxyl group, a sulfone group, a carboxyl group esterified with $C_1$–$C_6$-alkyl or benzyl or a sulfone group esterified with $C_1$–$C_6$-alkyl or benzyl, or an aralkyl group of up to 16 C-atoms substituted by a carboxyl group, a sulfone group, a carboxyl group esterified with $C_1$–$C_6$-alkyl or benzyl, or a sulfone group esterified with $C_1$–$C_6$-alkyl or benzyl, $R^3$ is H or a saturated, unsaturated, straight-chain or branched-chain or cyclic non-aromatic hydrocarbyl group with up to 20 C-atoms, which is optionally substituted by a carboxyl group, a sulfone group, a carboxyl group esterified with $C_1$–$C_6$-alkyl or benzyl, or a sulfone group esterified with $C_1$–$C_6$-alkyl or benzyl, an aryl group of up to 10 C-atoms which is optionally substituted by a carboxyl group, a sulfone group, a carboxyl group esterified with $C_1$–$C_6$-alkyl or benzyl, or a sulfone group esterified with $C_1$–$C_6$-alkyl or benzyl, or an aralkyl group of up to 16 C-atoms optionally substituted by a carboxyl group, a sulfone group, a carboxyl group esterified with $C_1$–$C_6$-alkyl or benzyl, or a sulfone group esterified with $C_1$–$C_6$-alkyl or benzyl, X is H and/or a metal ion equivalent of an element of atomic numbers 21–29, 31, 32, 37–40, 42–44, 49 or 57–83, wherein acid groups are, in each case, optionally present as an ester with $C_1$–$C_6$-alkyl, benzyl or 4-methoxybenzyl, or as an amide wherein the nitrogen atom of said amide is substituted by at least one saturated or unsaturated straight-chain, branched-chain or cyclic hydrocarbon radical with up to 5 C atoms, wherein said at least one hydrocarbon radical is optionally substituted by 1–3 hydroxy groups and/or 1–3 $C_1$–$C_4$-hydroxy groups, or said amide is in the form of a 5- or 6-membered heterocyclic ring with inclusion of the amide nitrogen atom; or a salt thereof with an inorganic and/or organic base, an amino acid or an amino acid amide, wherein at least two of substituents X are metal ion equivalents of at least one element of atomic numbers 21–29, 42, 44 or 57–83, at least one of substituents $Z^1$ and $Z^2$ is H, and, if n and l are each 0, then k and r are not both 1.

12. A method of radiodiagnostic imaging comprising imaging a patient to whom a contrast agent has been administered, the improvement wherein said contrast agent is a physiologically acceptable chelate compound of formula I $$\begin{array}{c} XOOCCH_2 \quad Z^1 \quad Z^2 \quad CH_2COOX \quad CH_2CON{<}^{R^2}_{R^3} \\ | \quad\quad | \quad | \quad | \quad\quad\quad | \\ N{-}{-}CH{-}CH{-}N{-}CH_2{-}CH_2{-}N \\ | \quad\quad\quad\quad\quad\quad\quad\quad\quad\quad | \\ XOOCCH_2 \quad\quad\quad\quad\quad\quad CH_2COOX \end{array} \quad (I)$$

wherein $Z^1$ and $Z^2$ are each, independently, H or —$(CH_2)_m$—$(C_6H_4)_q$—$(O)_k$—$(CH_2)_n$—$(C_6H_4)_l$—$(O)_r$—R, m and n are each independently 0–20, k, l, q and r are each independently 0 or 1, and R is H, $C_1$–$C_6$-alkyl, $C_1$–$C_6$-alkyl substituted by $OR^1$, or $CH_2COOR^1$,

21

R¹ is H, C₁–C₆-allyl, or benzyl,

R² is a saturated, unsaturated, straight-chain or branched-chain or cyclic non-aromatic hydrocarbyl group with up to 20 C-atoms which is substituted by a carboxyl group, a sulfone group, a carboxyl group esterified with C₁–C₆-alkyl or benzyl, or a sulfone group esterified with C₁–C₆-alkyl or benzyl,
  an aryl group of up to 10 C-atoms substituted by a carboxyl group, a sulfone group, a carboxyl group esterified with C₁–C₆-alkyl or benzyl or a sulfone group esterified with C₁–C₆-alkyl or benzyl, or
  an aralkyl group of up to 16 C-atoms substituted by a carboxyl group, a sulfone group, a carboxyl group esterified with C₁–C₆-alkyl or benzyl, or a sulfone group esterified with C₁–C₆-alkyl or benzyl, R³ is H or a saturated, unsaturated, straight-chain or branched-chain or cyclic non-aromatic hydrocarbyl group with up to 20 C-ators, which is optionally substituted by a carboxyl group, a sulfone group, a carboxyl group esterified with C₁–C₆-alkyl or benzyl, or a sulfone group esterified with C₁–C₆-alkyl or benzyl,
  an aryl group of up to 10 C-atoms which is optionally substituted by a carboxyl group, a sulfone group, a carboxyl group esterified with C₁–C₆-alkyl or benzyl, or a sulfone group esterified with C₁–C₆-alkyl or benzyl, or
  an aralkyl group of up to 16 C-atoms optionally substituted by a carboxyl group, a sulfone group, a carboxyl group esterified with C₁–C₆-alkyl or benzyl, or a sulfone group esterified with C₁–C₆-alkyl or benzyl, X is H and/or a metal ion equivalent of a radionuclide of atomic numbers 27, 29, 31, 32, 37–39, 43, 49, 62, 64, 70 or 77 wherein acid groups are, in each case, optionally present as an ester with C₁–C₆-alkyl, benzyl or 4-methoxybenzyl, or as an amide wherein the nitrogen atom of said amide is substituted by at least one saturated or unsaturated straight-chain, branched-chain or cyclic hydrocarbon radical with up to 5 C atoms, wherein said at least one hydrocarbon radical is optionally substituted by 1–3 hydroxy groups and/or 1–3 C₁–C₄-hydroxy groups, or said amide is in the form of a 5- or 6-membered heterocyclic ring with inclusion of the amide nitrogen atom; or a salt thereof with an inorganic and/or organic base, an amino acid or an amino acid amide, wherein at least one of substituents Z¹ and Z² is H, and, if n and l are each 0, then k and r are not both 1.

13. In a method of radiation therapy comprising administering a radiotherapeutic agent to a patient, the improvement wherein said agent is a physiologically acceptable chelate compound of formula I

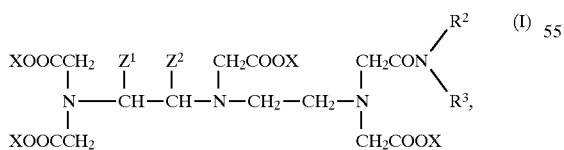

wherein

Z¹ and Z² are each independently H or —(CH₂)_m—(C₆H₄)_q—(O)_k—(CH₂)_n—(C₆H₄)_l—(O)_r—R, m and n are each independently 0–20, k, l, q and r are each independently 0 or 1, and R is H, C₁–C₆-alkyl, C₁–C₆-alkyl substituted by OR¹, or CH₂COOR¹,

22

R¹ is H, C₁–C₆-alkyl, or benzyl,

R² is a saturated, unsaturated, straight-chain or branched-chain or cyclic non-aromatic hydrocarbyl group with up to 20 C-atoms which is substituted by a carboxyl group, a sulfone group, a carboxyl group esterified with C₁–C₆-alkyl or benzyl, or a sulfone group esterified with C₁–C₆-alkyl or benzyl,
  an aryl group of up to 10 C-atoms substituted by a carboxyl group, a sulfone group, a carboxyl group esterified with C₁–C₆-alkyl or benzyl or a sulfone group esterified with C₁–C₆-alkyl or benzyl, or
  an aralkyl group of up to 16 C-atoms substituted by a carboxyl group, a sulfone group, a carboxyl group esterified with C₁–C₆-alkyl or benzyl, or a sulfone group esterified with C₁–C₆-alkyl or benzyl, R³ is H or a saturated, unsaturated, straight-chain or branched-chain or cyclic non-aromatic hydrocarbyl group with up to 20 C-atoms, which is optionally substituted by a carboxyl group, a sulfone group, a carboxyl group esterified with C₁–C₆-alkyl or benzyl, or a sulfone group esterified with C₁–C₆-alkyl or benzyl,
  an aryl group of up to 10 C-atoms which is optionally substituted by a carboxyl group, a sulfone group, a carboxyl group esterified with C₁–C₆-alkyl or benzyl, or a sulfone group esterified with C₁–C₆-alkyl or benzyl, or
  an aralkyl group of up to 16 C-atoms optionally substituted by a carboxyl group, a sulfone group, a carboxyl group esterified with C₁–C₆-alkyl or benzyl, or a sulfone group esterified with C₁–C₆-alkyl or benzyl, X is H and/or a metal ion equivalent of an element of atomic numbers 21–29, 31, 32, 37–40, 42–44, 49 or 57–83, wherein acid groups are, in each case, optionally present as an ester with C₁–C₆-alkyl, benzyl or 4-methoxybenzyl, or as an amide wherein the nitrogen atom of said amide is substituted by at least one saturated or unsaturated straight-chain, branched-chain or cyclic hydrocarbon radical with up to 5 C atoms, wherein said at least one hydrocarbon radical is optionally substituted by 1–3 hydroxy groups and/or 1–3 C₁–C₄-hydroxy groups, or said amide is in the form of a 5- or 6-membered heterocyclic ring with inclusion of the amide nitrogen atom; or a salt thereof with an inorganic and/or organic base, an amino acid or an amino acid amide, wherein at least one radionuclide is an element of atomic numbers 27, 29, 31, 32, 37–39, 43, 49, 62, 64, 70 or 77, at least one of substituents Z¹ and Z² is H, and, if n and l are each 0, then k and r are not both 1.

14. A method according to claim 1, wherein R² is 4-carboxy-phenylene, 1-cyclohexyl-1-carboxylic acid, 1-cyclopentyl-1-carboxylic acid, 2-carboxy-phenylene, 11-carboxy-1-undecyl, 10-carboxy-1-decyl, 7-carboxy-1-heptyl, 6-carboxy-1-hexyl, 5-carboxy-1-pentyl, 4-carboxy-benzyl, 4-carboxy-1-cyclohexylmethyl, 4-carboxymethyl-phenylene, 4-(1,1-dimethylcarboxymethylene)-phenylene, 4-sulfophenylene, 10-sulfo-1-decyl, 8-sulfo-1-octyl, 17-carboxy-7-heptadecyl, 7-carboxy-2-heptyl, 1-carboxy-4-phenyl-2-propyl, 2-carboxyethyl, or 4-carboxy-4-but-1-enyl.

15. A method according to claim 6, wherein R² is 4-carboxy-phenylene, 1-cyclohexyl-1-carboxylic acid, 1-cyclopentyl-1-carboxylic acid, 2-carboxy-phenylene, 11-carboxy-1-undecyl, 10-carboxy-1decyl, 7-carboxy-1-heptyl, 6-carboxy-1-hexyl, 5-carboxy-1-pentyl, 4-carboxybenzyl, 4-carboxy-1-cyclohexylmethyl, 4-carboxymethyl-phenylene, 4-(1,1-dimethylcarboxymethylene)-phenylene, 4-sulfophenylene, 10-sulfo-1-decyl, 8-sulfo-1-octyl, 17-carboxy-7-heptadecyl, 7-carboxy-2-heptyl, 1-carboxy-4-phenyl-2-propyl, 2-carboxyethyl, or 4-carboxy-4-but-1-enyl.

16. In a method of NMR imaging comprising imaging a patient to whom a contrast agent has been administered, the improvement wherein:

the patient's gastrointestinal tract, renal system, and/or hepatobiliary system is imaged, and said contrast agent is a physiologically acceptable chelate compound of formula

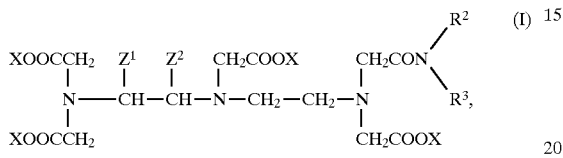

wherein $Z^1$ and $Z^2$ are each, independently, H or $-(CH_2)_m-(C_6H_4)_q-(O)_k-(CH_2)_n-(C_6H_4)_l-(O)_r-R$, m and n are each independently 0–20, k, l, q and r are each independently 0 or 1, and R is H, $C_1$–$C_6$-alkyl, $C_1$–$C_6$-alkyl substituted by $OR^1$, or $CH_2COOR^1$, $R^1$ is H, $C_1$–$C_6$-alkyl, or benzyl, $R^2$ is a saturated, unsaturated, straight-chain or branched-chain or cyclic non-aromatic hydrocarbyl group with up to 20 C atoms which is substituted by a carboxyl group, a sulfone group, a carboxyl group esterified with $C_1$–$C_6$-alkyl or benzyl, or a sulfone group esterified with $C_1$–$C_6$-alkyl or benzyl, an aryl group of up to 10 C atoms substituted by a carboxyl group, a sulfone group, a carboxyl group esterified with $C_1$–$C_6$-alkyl or benzyl or a sulfone group esterified with $C_1$–$C_6$-alkyl or benzyl, or an aralkyl group of up to 16 C atoms substituted by a carboxyl group, a sulfone group, a carboxyl group esterified with $C_1$–$C_6$-alkyl or benzyl, or a sulfone group esterified with $C_1$–$C_6$-alkyl or benzyl, $R^3$ is H or a saturated, unsaturated, straight-chain or branched-chain or cyclic non-aromatic hydrocarbyl group with up to 20 C atoms, which is substituted by a carboxyl group, a sulfone group, a carboxyl group esterified with $C_1$–$C_6$-alkyl or benzyl, or a sulfone group esterified with $C_1$–$C_6$-alkyl or benzyl, an aryl group of up to 10 C atoms which is substituted by a carboxyl group, a sulfone group, a carboxyl group esterified with $C_1$–$C_6$-alkyl or benzyl, or a sulfone group esterified with $C_1$–$C_6$-alkyl or benzyl, or an aralkyl group of up to 16 C atoms substituted by a carboxyl group, a sulfone group, a carboxyl group esterified with $C_1$–$C_6$-alkyl or benzyl, or a sulfone group esterified with $C_1$–$C_6$-alkyl or benzyl, X is H and/or a metal ion equivalent of an element of atomic numbers 21–29, 31, 32, 37–40, 42–44, 49 or 57–83, wherein acid groups are, in each case, optionally present as an ester, or as an amide;

a salt thereof with an inorganic and/or organic base, an amino acid or an amino acid amide, wherein at least two of substituents X are metal ion equivalents of at least one element of atomic numbers 21–29, 42, 44 or 58–70, at least one of substituents $Z^1$ and $Z^2$ is H, and, if n and l are each 0, then k and r are not both 1.

17. A method according to claim 16, wherein one of $Z^1$ and $Z^2$ is H and the other is $-CH_2-C_6H_4-OH$, $-CH_2-C_6H_4-OCH_3$, $-CH_2C_6H_5$, $-CH_2-C_6H_4-O-CH_2-C_6H_4-OCH_3$, $-CH_2-O-CH_2-C_6H_5$, $-CH_2-C_6H_4-O-CH_2-COOH$, $-CH_2-C_6H_4-OC_2H_5$, $-CH_2-C_6H_4-OC_4H_9$, $-CH_2-C_6H_4-O-CH_2-C_6H_5$.

18. A method according to claim 16, wherein $R^3$ stands for the methyl, ethyl, propyl, isopropyl, butyl, pentyl, hexyl, phenyl, benzyl, 4-carboxy-phenylene, 1-cyclohexyl-1-carboxylic acid, 1-cyclopentyl-1-carboxylicacid, 2-carboxy-phenylene, 11-carboxy-1-undecyl, 10-carboxy-1-decyl, 7-carboxy-1-heptyl, 6-carboxy-1-hexyl, 5-carboxy-1-pentyl, 4-carboxybenzyl, 4-carboxy-1-cyclohexylmethyl, 4-carboxymethyl-phenylene, 4-(1,1-dimethylcarboxymethylene)-phenylene, 4-sulfophenylene, 10-sulfo-1-decyl, 8-sulfo-1-octyl, 17-carboxy-7-heptadecyl, 7-carboxy-2-heptyl, 1-carboxy-4-phenyl-2-propyl, 2-carboxyethyl, 4-carboxy-4-but-1-enyl radical.

* * * * *